United States Patent

Kurohashi et al.

Patent Number: 5,446,021
Date of Patent: Aug. 29, 1995

[54] AGRICULTURAL AND HORTICULTURAL COMPOSITIONS INDUCING RESISTANCE IN PLANTS AGAINST SALT- AND WATER-STRESS

[75] Inventors: Masaharu Kurohashi; Ko Nakamura; Kazuharu Ienaga, all of Hyogo, Japan

[73] Assignee: Nippon Zoki Pharmaceutical Co., Ltd., Osaka, Japan

[21] Appl. No.: 240,534

[22] Filed: May 10, 1994

Related U.S. Application Data

[63] Continuation of Ser. No. 807,756, Dec. 17, 1991, abandoned, which is a continuation of Ser. No. 632,662, Dec. 27, 1990, abandoned, which is a continuation of Ser. No. 316,620, Feb. 28, 1989, abandoned.

[30] Foreign Application Priority Data

Mar. 1, 1988 [JP] Japan .................................. 63-49117

[51] Int. Cl.⁶ ............................................. A61K 38/12
[52] U.S. Cl. ......................................... 514/9; 514/10
[58] Field of Search ............... 514/9, 10, 11; 504/116, 504/136; 47/58, 16; 544/282, 252

[56] References Cited

PUBLICATIONS

Ienaga et al, Tetrahedron Letters, vol. 28, No. 12, pp. 1285-1286 (1987).
JP 202379 Apr. 29, 1984 Abstract.
Ueda, et al. (1985) Int. J. Peptide Protein Research 25: 475-480.
Sleeckx, et al. (1985) Bull. Soc. Chim. Belg. 94: 187-198. Abstracted Mar. 31, 1986.

*Primary Examiner*—Che S. Chereskin
*Attorney, Agent, or Firm*—Armstrong, Westerman, Hattori, McLeland & Naughton

[57] ABSTRACT

The present invention relates to an agricultural and horticultural composition inducing resistance in plants against salt- and water-stresses which comprises as an active ingredient an effective amount of at least one cyclic dipeptide of the following formula (I) or an agriculturally or horticulturally acceptable salt thereof;

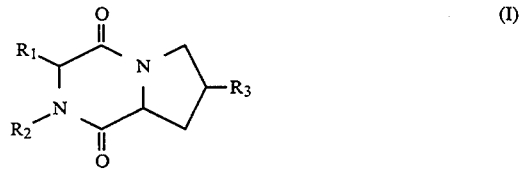

wherein each of $R_1$ and $R_2$, which may be the same or different, is a hydrogen atom or lower alkyl group, or $R_1$ and $R_2$ are joined to form pyrrolidine ring which may optionally have hydroxy group, and $R_3$ is a hydrogen atom or hydroxy group.

9 Claims, 1 Drawing Sheet

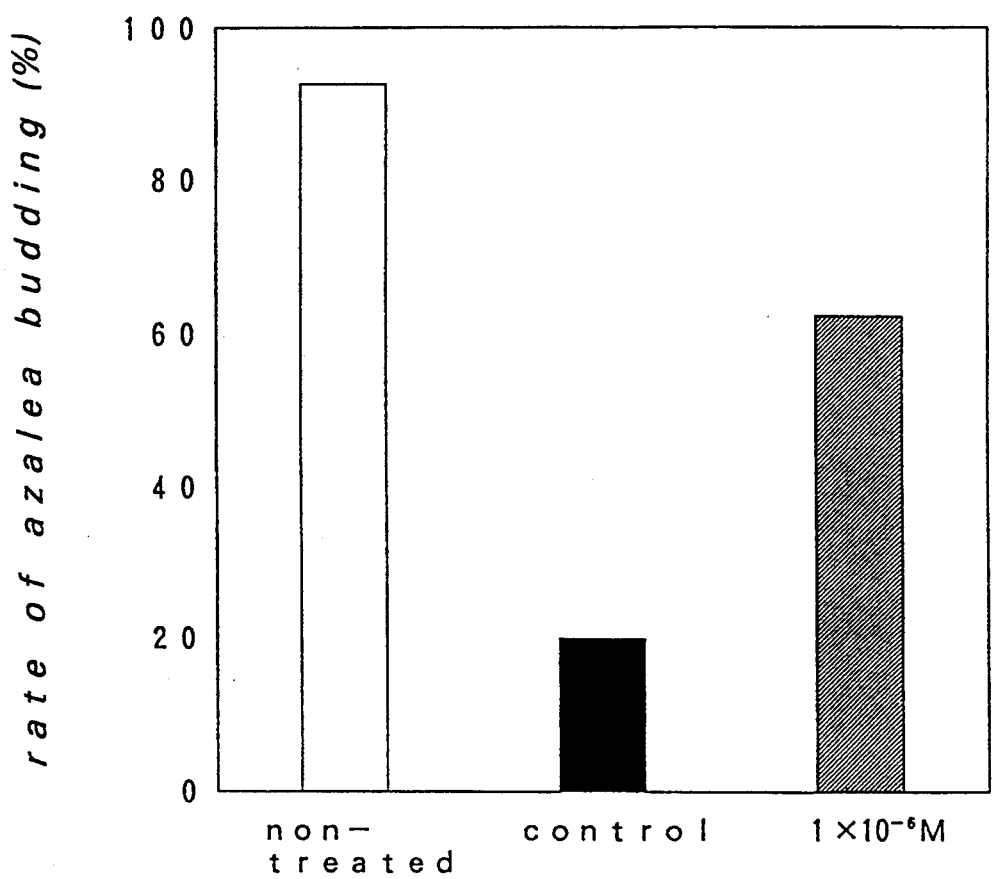

AGRICULTURAL AND HORTICULTURAL COMPOSITIONS INDUCING RESISTANCE IN PLANTS AGAINST SALT- AND WATER-STRESS

This application is a continuation of application Ser. No. 07/807,756 filed Dec. 17, 1991, is now abandoned which is a continuation of application Ser. No. 632,662 filed Dec. 27, 1990, now abandoned which is a continuation of application Ser. No. 316,620 filed Feb. 28, 1989, now abandoned.

The present invention relates to agricultural and horticultural compositions, particularly compositions inducing resistance in plants against salt- and water-stresses.

In various factors damaging plants, a drought and salt damage in a region closed by a coast are a kind of damaging factor mainly causing obstruction to plant growth by abnormal osmotic pressure at a site of root. Under these undesirable environments, plants fall into the state of salt- and/or water-stresses. There is thus a need for substances having normalizing effect on the germination of plant under salt- and water-stresses to prevent a decrease in agricultural yields and injury of garden plants. Certain cyclic dipeptides having excellent effects inducing resistance in plants against salt- and water-stresses have accordingly been found.

An object of the present invention is to provide agricultural and horticultural compositions comprising as an active ingredient an effective amount of at least one cyclic dipeptide, particularly compositions inducing resistance in plants against salt- and water-stresses. Another object of the invention is to provide a use of a cyclic dipeptide of the present invention to induce resistance in plants against the said stresses.

BRIEF DESCRIPTION OF THE INVENTION

The agricultural and horticultural compositions of the present invention comprising as an active ingredient an effective amount of at least one cyclic dipeptide of the following formula (I) or an agriculturally or horticulturally acceptable salt thereof.

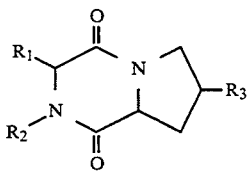

wherein each of $R_1$ and $R_2$, which may be the same or different, is a hydrogen atom or lower alkyl group, or $R_1$ and $R_2$ are joined to form pyrrolidine ring which may optionally have hydroxy group, and $R_3$ is a hydrogen atom or hydroxy group.

In the above formula (I), each of $R_1$ and $R_2$, which may be the same or different, is a hydrogen atom or lower alkyl group, preferably a straight or branched alkyl group having 1 to 5 carbon atoms, such as methyl, ethyl, propyl, isopropyl, butyl, isobutyl, sec-butyl, tert-butyl, pentyl, isopentyl, neopentyl or tert-pentyl, or $R_1$ and $R_2$ are joined to form pyrrolidine ring which may optionally have hydroxy group, and $R_3$ is a hydrogen atom or hydroxy group.

The compounds of the formula (I) in the present application are represented using the abbreviations of amino acids which are adopted by IUPAC and IUB or are commonly used in the art to which the present invention pertains.

The following abbreviations of amino acids and substituent groups are used.
Pro: proline
Ala: alanine
I/e: isoleucine
Leu: leucine
Hyp: hydroxyproline
Me: methyl group
nBu: n-butyl group The amino acid residue in the present invention may be any of the D-isomer, L-isomer and DL-isomer. Also aHyp represents the trans-isomer of Hyp between the headbridge hydrogen and hydroxy group.

For example, cyclo[D-(Me)Leu-L-Hyp] is the cyclic dipeptide represented by the following formula.

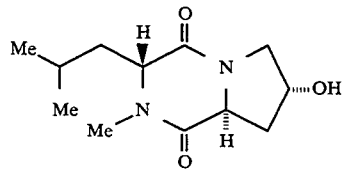

Preferred cyclic dipeptides of the present invention include:
Cyclo(L-Ala-L-Pro)
Cyclo(L-Leu-L-Pro)
Cyclo(L-Ala-L-Hyp)
Cyclo(L-Ile-L-Hyp)
Cyclo(L-Leu-L-Hyp)
Cyclo[L-(N-Me)Leu-L-Hyp]
Cyclo[D-(N-Me)Leu-L-Hyp]
Cyclo[D-(N-nBu)Leu-L-Hyp]
Cyclo(L-Pro-L-Hyp)
Cyclo(D-Pro-D-aHyp)
Cyclo(D-Pro-D-Hyp)
Cyclo(L-Pro-L-aHyp)
Cyclo(L-Hyp-L-Hyp)
Cyclo(L-aHyp-L-aHyp)
±Cyclo(Pro-Pro)

The cyclic dipeptides of the present invention also include agriculturally or horticulturally acceptable salts of the compounds of the above formula (I), for example, salts with alkali metal such as sodium or potassium, with alkaline-earth metal such as calcium, magnesium or barium, or with other metals such as aluminum and the like; salts with an acid such as hydrochloric acid, sulfuric acid, nitric acid, phosphoric acid, hydrobromic acid, trifluoroacetic acid, formic acid, acetic acid, citric acid or lactic acid; or salts with an organic base such as ammonia or organic amine.

These salts can be produced from free cyclic dipeptides in the usual way or can be interchanged with each other.

BRIEF DESCRIPTION OF THE DRAWING

FIG. 1 is a graph illustrating the effect a cyclic dipeptide (compound 9) in protecting azaleas against salt-stress.

DETAILED DESCRIPTION OF THE INVENTION

The above cyclic dipeptides are known compounds, e.g. the compounds disclosed in the prior literatures, and so the compounds according to the present invention can be produced by art-recognized methods as follows:

(1) Both of the two amino acids, such as Pro, Hyp, Ala, Leu, Ile and their derivatives having a lower alkyl group, which constitute the cyclic dipeptides of the present invention are reacted in an appropriate solvent such as water or ethylene glycol at room temperature or, if desired, by heating to higher temperature to give the desired compounds of the invention.

(2) In an appropriate solvent such as methylene chloride which does not inhibit the reaction, Pro or Hyp of which hydroxy group is protected by a conventional hydroxy-protecting group such as n-butyl are condensed with Pro or Hyp of which hydroxy group is protected, or with Ala, Leu or Ile having a conventional amino-protecting group such as benzyloxycarbonyl by the use of a condensing agent such as dicyclohexylcarbodiimide. After the condensation reaction, cyclization of the dipeptide can be carried out simultaneously with removal of protecting group, for example, catalytic reduction using palladium-carbon, to give the cyclic dipeptides of the present invention.

(3) The compounds having a lower alkyl group as a substituent $R_2$ can be produced by a conventional alkylation, for example, the hydroxy group of Hyp is protected by a hydroxy-protecting group such as tetrahydrofuran, and then reacted with an alkylating agent such as alkylhalide to introduce a lower alkyl group into the $R_2$ position.

The resulting compounds of the present invention can be purified by known methods such as distillation, chromatography and recrystallization. Identification is established through, inter alia, melting point, elemental analysis, IR, NMR, UV, mass spectrum, etc. The specific rotatory power was measured using a sodium lamp ($\lambda = 5893 Å$).

EXAMPLES

According to the above-mentioned methods of the cyclic dipeptides, the following compounds of the present invention were prepared.

[Compound 1] Cyclo (L-Ala-L-Pro) m.p.: 179°–184° C. $[\alpha]^{24}$: −142.5° (C=1, methanol)

[Compound 2] Cyclo (L-Leu-L-Pro) m.p.: 164°–167° C. $[\alpha]^{24}$: −131.7° (C=1, methanol )

[Compound 3] Cyclo (L-Ala-L-Hyp) m.p.: 205°–210° C. $[\alpha]^{25}$: −150.7° (C=1, methanol)

[Compound 4] Cyclo(L-Ile-L-Hyp) m.p.: 161.5°–162° C. $[\alpha]^{25}$: −152.5° (C=1, water)

Compound 5] Cyclo (L-Leu-L-Hyp) m.p.: 178°–179° C. $[\alpha]^{25}$: −148.2° (C=1, water)

Compound 6] Cyclo(L-(N-Me)Leu-L-Hyp) m.p.: oily substance $[\alpha]^{25}$: −88.7° (C=1.2, methanol)

Compound 7] Cyclo (D-(N-Me)Leu-L-Hyp) m.p.: oily substance $[\alpha]^{25}$: +55.8° (C=1, methanol)

Compound 8] Cyclo(D-(N-nBu)Leu-L-Hyp) m.p.: 112°–114° C. $[\alpha]^{25}$: +88.0° (C=1.1, methanol)

Compound 9] Cyclo(L-Pro-L-Hyp) m.p.: 141°–142° C. $[\alpha]^{28}$: −134.4° (C=1, methanol)

Compound 10] Cyclo(D-Pro-D-aHyp) m.p.: 174°–175 ° C. $[\alpha]^{28}$: +90.8° (C=1, methanol)

Compound 11] Cyclo(D-Pro-D-Hyp) m.p.: 141°–142 ° C. $[\alpha]^{28}$: +134.0° (C=1, methanol)

Compound 12] Cyclo(L-Pro-L-aHyp) m.p.: 175°–176° C. $[\alpha]^{28}$: −90.4° (C=1, methanol)

Compound 13] Cyclo(L-Hyp-L-Hyp)

Compound 14] Cyclo(L-aHyp-L-aHyp)

Compound 15] ±Cyclo(Pro-Pro)

The following descriptions serve to illustrative agricultural and horticultural studies of the compounds of the present invention.

(I) Effects on rice seedlings under salt-stress caused by sodium chloride (NaCl)

A filter paper soaked with an aqueous solution of a test agent was laid in a germination dish. Even-sized seeds of rice (*Oryza sativa* L. *japonica*) were selected, washed with an aqueous solution containing 0.5% Tween 20 and 1.0% sodium hypochlorite, and then dried. The gemination dishes were sowed with the said rice seeds.

The seeds were treated with the aqueous solution of the test agent only during the germination period (4 days). The five seeds having equal root lengths were transplanted from germination dishes to water culture vessels with/without NaCl-solution, not containing any test drug. Lengths and weights of both shoots and roots were measured 7 days after transplantation.

These tests (30° C., 24 h daylight) were repeated 6 times, and the mean value and standard error (S.E.) were obtained.

TABLE 1

|  | Shoot length (mm) | Root length (mm) |
|---|---|---|
| 0% NaCl | 71.2 ± 1.60 | 57.3 ± 3.29 |
| 0.1% NaCl | 78.0 ± 1.74 | 53.3 ± 2.61 |
| 0.2% NaCl | 77.6 ± 1.63 | 39.7 ± 2.02 |
| 0.3% NaCl | 79.2 ± 1.48 | 37.8 ± 1.48 |
| 0.5% NaCl | 45.3 ± 1.82 | 33.8 ± 1.76 |
| 0.75% NaCl | 34.7 ± 0.66 | 32.9 ± 1.07 |
| 1.0% NaCl | 28.2 ± 0.47 | 34.0 ± 1.75 |

Table 1 shows that the rice growth are apparently inhibited by NaCl in the medium.

The effects of the compounds of the present invention inducing resistance in rice against salt-stress are described below:

TABLE 2

| Concentration of Compound 2 (M) | Shoot length (mm) | Root length (mm) |
|---|---|---|
| 1.0% NaCl | | |
| control | 28.8 ± 0.39 | 36.1 ± 1.45 |
| 1 × 10⁻⁴ | 30.4 ± 0.60 | 38.2 ± 1.60 |
| 1 × 10⁻¹⁰ | 31.1 ± 0.60 | 37.3 ± 1.69 |
| 1.5% NaCl | | |
| control | 20.2 ± 0.56 | 35.2 ± 1.52 |
| 1 × 10⁻⁴ | 22.3 ± 0.53 | 38.3 ± 1.89 |
| 1 × 10⁻¹⁰ | 21.9 ± 0.53 | 39.2 ± 2.11 |

TABLE 3

| Concentration of Compound 4 (M) | Shoot length (mm) | Root length (mm) |
|---|---|---|
| 1.0% NaCl | | |
| control | 20.7 ± 0.96 | 15.7 ± 0.85 |
| 5 × 10⁻⁶ | 30.9 ± 1.24 | 19.9 ± 0.60 |
| 5 × 10⁻⁸ | 27.1 ± 0.67 | 21.2 ± 0.68 |
| 1.5% NaCl | | |
| control | 12.3 ± 0.64 | 12.1 ± 0.42 |
| 5 × 10⁻⁸ | 16.0 ± 0.75 | 14.9 ± 0.52 |
| 5 × 10⁻¹⁰ | 16.3 ± 0.66 | 14.7 ± 0.52 |

TABLE 4

| Concentration of Compound 5 (M) | Shoot length (mm) | Root length (mm) |
|---|---|---|
| 1.0% NaCl | | |
| control | 20.7 ± 0.96 | 15.7 ± 0.85 |

TABLE 4-continued

| Concentration of Compound 5 (M) | Shoot length (mm) | Root length (mm) |
| --- | --- | --- |
| $5 \times 10^{-4}$ | 28.7 ± 0.87 | 19.7 ± 0.69 |
| $5 \times 10^{-8}$ | 25.4 ± 0.83 | 20.5 ± 0.87 |
| 1.5% NaCl | | |
| control | 12.3 ± 0.64 | 12.1 ± 0.42 |
| $5 \times 10^{-4}$ | 17.1 ± 0.76 | 13.9 ± 0.61 |
| $5 \times 10^{-8}$ | 15.6 ± 0.28 | 15.7 ± 0.58 |

TABLE 5

| Concentration of Compound 9 (M) | Shoot length (mm) | Root length (mm) |
| --- | --- | --- |
| 1.0% NaCl | | |
| control | 20.7 ± 0.96 | 15.7 ± 0.85 |
| $5 \times 10^{-4}$ | 28.8 ± 0.99 | 19.5 ± 0.96 |
| $5 \times 10^{-8}$ | 27.1 ± 0.83 | 21.8 ± 0.86 |
| 1.5% NaCl | | |
| control | 12.3 ± 0.64 | 12.1 ± 0.42 |
| $5 \times 10^{-6}$ | 17.3 ± 0.42 | 15.9 ± 0.44 |
| $5 \times 10^{-10}$ | 16.0 ± 0.64 | 14.0 ± 0.49 |

TABLE 6

| Concentration of Compound 13 (M) | Shoot length (mm) | Root length (mm) |
| --- | --- | --- |
| 1.0% NaCl | | |
| control | 27.3 ± 0.55 | 29.2 ± 1.96 |
| $1 \times 10^{-6}$ | 29.4 ± 0.61 | 38.5 ± 1.66 |
| $1 \times 10^{-8}$ | 30.5 ± 0.59 | 38.1 ± 2.03 |
| 1.5% NaCl | | |
| control | 20.5 ± 0.40 | 31.3 ± 1.65 |
| $1 \times 10^{-4}$ | 21.4 ± 0.69 | 35.6 ± 2.28 |
| $1 \times 10^{-8}$ | 21.9 ± 0.40 | 37.9 ± 1.58 |

TABLE 7

| Concentration of Compound 14 (M) | Shoot length (mm) | Root length (mm) |
| --- | --- | --- |
| 1.0% NaCl | | |
| control | 27.3 ± 0.55 | 29.2 ± 1.96 |
| $1 \times 10^{-6}$ | 31.8 ± 0.57 | 43.2 ± 1.69 |
| $1 \times 10^{-10}$ | 30.4 ± 0.60 | 38.2 ± 1.57 |
| 1.5% NaCl | | |
| control | 20.5 ± 0.40 | 31.3 ± 1.65 |
| $1 \times 10^{-4}$ | 21.8 ± 0.58 | 35.0 ± 1.77 |
| $1 \times 10^{-10-6}$ | 22.6 ± 0.83 | 35.3 ± 1.93 |

TABLE 8

| Concentration of Compound 15 (M) | Shoot length (mm) | Root length (mm) |
| --- | --- | --- |
| 1.5% NaCl | | |
| control | 21.9 ± 0.50 | 39.0 ± 1.76 |
| $1 \times 10^{-6}$ | 24.2 ± 0.50 | 42.7 ± 1.65 |

(II) Effects on rice seedlings under water-stress caused by mannitol

Using mannitol instead of NaCl in the similar manner (I) as mentioned above, the effects of the compounds of the present invention inducing resistance against water-stress were studied. An example of the results is shown in Table 9.

TABLE 9

| Concentration of Compound 9 (M) | (25° C., 14 h daylight) | |
| --- | --- | --- |
| | Shoot length (mm) | Root length (mm) |
| 2.5% mannitol | | |
| control | 55.3 ± 7.74 | 40.7 ± 22.73 |

TABLE 9-continued

| Concentration of Compound 9 (M) | (25° C., 14 h daylight) | |
| --- | --- | --- |
| | Shoot length (mm) | Root length (mm) |
| $1 \times 10^{-4}$ | 70.2 ± 3.73 | 67.7 ± 23.84 |
| $1 \times 10^{-8}$ | 63.4 ± 2.18 | 68.2 ± 10.42 |
| 5.0% mannitol | | |
| control | 26.4 ± 2.43 | 29.3 ± 10.51 |
| $1 \times 10^{-4}$ | 30.0 ± 2.29 | 39.6 ± 1.80 |
| $1 \times 10^{-8}$ | 27.1 ± 1.55 | 46.7 ± 9.51 |

(III) Effects on tomato seedlings under salt-stress caused by NaCl

Tomato seeds were treated with the aqueous solution of the test agent during the germination period (4 days). 9 days after transplantation from germination dishes to water culture vessels, 0.5% NaCl-solution was added to the vessels. The tomato seedlings had been cultivated for 22 days in the culture medium containing NaCl. An example of the results is shown in Table 10.

TABLE 10

| Concentration of Compound 9 (M) | (25~30° C., 12 h daylight, n = 12~18) Dried stem and leaves weight (mg) |
| --- | --- |
| 0% NaCl | |
| control | 156.9 ± 13.4 |
| 0.5% NaCl | |
| control | 80.2 ± 7.6 |
| $1 \times 10^{-6}$ | 111.4 ± 8.8 |
| $1 \times 10^{-8}$ | 141.4 ± 14.4 |

(IV) Effects on cucumber seedlings under salt-stress caused by NaCl

Cucumber seeds were treated with the aqueous solution of the test agent during the germination period (3 days). 11 days after transplantation from germination dishes to water culture vessels, 0.5% NaCl-solution was added to the vessels. The cucumber seedlings had been for 25 days cultivated in the culture medium containing NaCl. An example of the results is shown in Table 11.

TABLE 11

| Concentration of Compound 9 (M) | (25~32° C., 12 h daylight, n = 5) Dried stem weight (mg) |
| --- | --- |
| 0% NaCl | |
| control | 151.7 ± 11.36 |
| 0.5% NaCl | |
| control | 81.9 ± 5.31 |
| $1 \times 10^{-6}$ | 104.9 ± 7.37 |
| $1 \times 10^{-8}$ | 95.5 ± 3.25 |

(V) Effect on azaleas under salt-stress caused by $CaCl_2$

Branches about 20 cm from the top of an azalea bush were cut off. The cuttings were dipped into 50 ml of water of the test solution (compound 9; $1 \times 10^{-6}$M) in a glass culture tube. The solution was replaced with new solution once a week. Six days after cutting of the branches, a 20% solution of $CaCl_2$, which has been used as an antifreezing agent, was sprayed on the cuttings. Thirty days after the $CaCl_2$ treatment, the rate of azalea budding was measured using the following equation:

$$\text{rate of azalea budding (\%)} = \frac{\text{the number of green buds}}{\text{the number of all buds}} \times 100$$

An example of the results in shown in FIG. 1.

As shown in FIG. 1, the compounds of the present invention can induce resistance in mature plants against salt-stress as well as in seeds during the germination period.

As shown by the above-mentioned results (Table 2 to 8), rice seeds treated with the compounds of the present invention added to the growth medium during the germination period had resistant effects against the growth inhibition by NaCl after the transplantation of rice seedlings from germination dishes to water culture vessels containing NaCl.

Also the compounds of the present invention induced resistance in other plants such as tomato (Table 10) and cucumber (Table 11) against salt-stress. Particularly in the case of tomato, seedlings not treated with the compounds of the invention were weak and fell down, on the other hand the seedlings treated with the present compounds had firm stems and so did not fall down as well as the group cultivated in the medium without NaCl.

Similarly the effect of the present compounds inducing resistance against the plant growth inhibition was observed when a sugar was used instead of NaCl (Table 9). Therefore, the seeds treated with the compounds of the present invention during the germination period have resistant effects against water-stress causing osmotically obstruction to the plant growth as well as against salt-stress.

By the treatment of the seeds of agricultural plants beforehand with the compounds of the present invention, though the plants are exposed to a drought or salt damage, they can resist salt- or water-stresses.

Therefore, agricultural and horticultural compositions comprising as an active ingredient an effect amount of at least one cyclic dipeptide of the present invention are very useful in regions where agricultural and horticultural plants fall into the state of salt- and/or water-stresses, for example, a salty region such as reclaimed land, coast land easily suffered from salt damage or a region closed by a desert susceptible to be damaged by a drought.

The effects inducing resistance in plants against salt- and water-stresses of the agricultural and horticultural compositions of the present invention can be achieved by treating seeds with a solution of the present composition during only the germination period. The cyclic dipeptide solution may be of any convenient concentration, preferably the concentration of from $1 \times 10^{-3}$ to $1 \times 10^{-11}$M, to treat seeds to induce resistance in plants against salt- and water-stresses. An effective results can be obtained even at low concentration, for example the concentration of from $1 \times 10^{-8}$ to $1 \times 10^{-10}$M, which is advantage economically.

What we claimed is:

1. A method of inducing resistance in plants against salt- and water-stress which comprises treating seeds and plants with a cyclic dipeptide of the formula

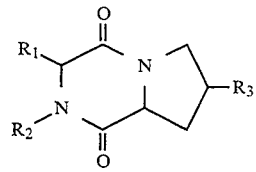

wherein $R_1$ is a $C_4$ alkyl group and $R_2$ is a hydrogen atom, or $R_1$ and $R_2$ are joined to form a pyrrolidine ring which may optionally have at least one hydroxy group substituent, and $R_3$ is a hydrogen atom or a hydroxy group; or an agriculturally or horticultually acceptable salt thereof.

2. A method according to claim 1, wherein $R_3$ is a hydrogen atom.

3. A method according to claim 1, wherein $R_3$ is a hydroxy group.

4. A method according to claim 1, wherein $R_1$ is a $C_4$ alkyl group.

5. A method according to claim 4, wherein $R_3$ is a hydrogen atom.

6. A method according to claim 4, wherein $R_3$ is a hydroxy group.

7. A method according to claim 1, wherein $R_1$ and $R_2$ are joined to form a pyrrolidine ring.

8. A method according to claim 7, wherein the pyrrolidine ring is substituted with a hydroxy group.

9. A method according to claim 1, wherein the cyclic dipeptide is cyclo (L-Leu-L-Pro), cyclo(L-Ile-L-Hyp), cyclo (L-Leu-L-Hyp), cyclo (L-Pro-L-Hyp), cyclo (L-Hyp-L-Hyp), cyclo (L-aHyp-L-aHyp) or ±cyclo (Pro-Pro).

* * * * *